United States Patent [19]

Staal

[11] 4,447,364
[45] May 8, 1984

[54] METHOD FOR THE PREPARATION OF LIQUID ALUMINUM CITRATE

[75] Inventor: Philip W. Staal, Elkhart, Ind.

[73] Assignee: Miles Laboratories, Inc., Elkhart, Ind.

[21] Appl. No.: 461,467

[22] Filed: Jan. 27, 1983

Related U.S. Application Data

[63] Continuation-in-part of Ser. No. 295,227, Aug. 21, 1981, which is a continuation-in-part of Ser. No. 153,766, May 27, 1980.

[51] Int. Cl.$^3$ .................. C07D 103/04; C07F 5/06
[52] U.S. Cl. ........................... 260/448 R; 260/448 B
[58] Field of Search ........................ 260/448 B, 448 R

[56] References Cited

U.S. PATENT DOCUMENTS

| | | | |
|---|---|---|---|
| 3,446,585 | 10/1963 | Tangbe | 260/448 R |
| 3,584,025 | 6/1971 | Boye et al. | 260/448 R |
| 3,762,476 | 10/1973 | Gall | 166/294 |
| 3,865,857 | 2/1975 | Suzuki et al. | 260/448 R |
| 3,959,093 | 5/1976 | Merki | 260/448 R |

FOREIGN PATENT DOCUMENTS 2758936  8/1978  Fed. Rep. of Germany .

OTHER PUBLICATIONS

*Chemical Abstracts*, vol. 89, #199106e, Montedison, "Tanning", 1978.
*Chemical Abstracts*, vol. 83, #167105p, Kwong et al, "Influence of Citric Acid on the Crystallization of Aluminum Hydroxide", 1975.
*Chemical Abstracts*, vol. 89, #164958q, Ancona et al., "Tanning Agent for Skins", 1978.

*Primary Examiner*—Natalie Trousof
*Assistant Examiner*—Raymond K. Covington
*Attorney, Agent, or Firm*—Jerome L. Jeffers

[57] ABSTRACT

Disclosed is a method for the preparation of a stable solution of aluminum citrate. The method involves combining a solution of aluminum chloride with a solution of citric acid while maintaining vigorous agitation. After formation of the aluminum citrate solution, sufficient alkali metal or ammonium hydroxide is added to increase the pH to a level of 5.5 to 7.5. During addition of the base, the agitation is continued and the temperature of the solution is maintained at a level of from 20° C. to 90° C.

7 Claims, No Drawings

METHOD FOR THE PREPARATION OF LIQUID ALUMINUM CITRATE

BACKGROUND OF THE INVENTION

This application is a continuation-in-part of co-pending application Ser. No. 295,227 filed Aug. 21, 1981 which is in turn a continuation-in-part of application Ser. No. 153,766 filed May 27, 1980.

The removal of oil from underground formations can be divided into 3 steps. The first step called primary recovery is to allow the oil to flow out of the ground, relying on natural forces or using a simple pumping technique to lift the oil to the surface. The life span of primary recovery operations for a well can vary from only a few years to 30 years or more, depending on the type of formation involved, the viscosity of the crude, the gas content of the oil and permeability of the reservoir. Under normal conditions, 5% to 25% of the oil in the formation is removed using primary recovery leaving a significant portion of the oil to be removed by more difficult and expensive techniques.

In some fields, the oil saturated formation is contiguous with a larger, porous, water containing formation called an aquifer. If this adjoining aquifer outcrops, it will have a continuous supply of salt brine which will feed into the oil reservoir, providing a constant drive to replace the oil removed. The result is as much as 30% of the oil being removed from the reservoir with the economic limit being reached when the oil-water mixture is so high in water that the oil produced does not pay for the pumping and separation costs.

Unfortunately, not all formations are of the above type and secondary recovery operations such as "water flooding" are necessary. In this operation, injection wells are drilled at intervals throughout the field and water is pumped into the oil-bearing formation to displace the oil towards the producing wells. This method has become very popular and results in average total recovery, using both primary and secondary techniques, of 30% to 33%.

The remaining oil, amounting to two thirds of the original volume, is the target of tertiary recovery techniques called "Enhanced Oil Recovery" or EOR. One of the first EOR techniques is steam flooding of reservoirs which contain highly viscous crude which is difficult or impossible to remove without raising its temperature to reduce its viscosity. This can be accomplished by injection of high pressure steam or causing underground combustion which results in crude thin enough to be pumped to the surface. Another less popular technique is to pump fluids that mix easily with the oil to the producing well. Light hydrocarbons have been used in this technique although liquefied $CO_2$ has gained wider favor. In practice, problems with efficiency and uniformity of the $CO_2$ sweep throughout the reservoir have retarded the widespread application of this technique.

A third technique for EOR that is presently gaining acceptance in the field is the use of chemicals and chemical processes to increase oil production. When the reservoir undergoes a water-flood, much of the oil remains behind attached to the walls of the capillary passages and trapped in the pores of the sandstone formation. The water-flood, always following the path of least resistance, bypasses or slides past the oil. A reduction in surface tension by the injection of chemicals can help break this oil loose from the formation. Adding only a surfactant or micellar dispersion, however, does not release much additional oil. After such investigation, several systems were developed to push the surfactant and oil through the formation in a uniform manner. Polymers such as polyacrylamide, carboxymethylcellulose and polysaccharides have been found to possess the desirable properties needed to act as a fluid piston and drive the oil towards the producer well. In practice, the micellar dispersion containing surfactant is pumped into the formation followed by the polymer, which is injected as a fairly linear, low-viscosity molecule in order to permeate the microscopic pores of the sandstone. The polymer is then thickened in the formation by introducing metal ions such as aluminum complexed as aluminum citrate to cross-link the polymer and form a gel. At this point, the gel is moved using water flooding techniques resulting in a sweep of the oil bank towards the producer well. This process is more fully described in U.S. Pat. No. 3,762,476 issued Oct. 2, 1973.

A second system, similar to the micellar polymer flood but different in its action, involves the injection of a cationic or anionic polymer, depending on the electrical charge of the sandstone in the formation, followed by aluminum citrate to cross-link and gel the polymer. The polymer, by virtue of its ionic charge, is attached to the capillary walls, thereby filling the voids and larger bypass pores while avoiding the smallest passages. The result is a more uniform pore size throughout the formation which results in increased oil production during water flooding.

Aluminum citrate is preferred for use as the cross-linking material because of its low cost and the slow release of aluminum which results in a relatively long period of activity after its injection into the formation. In a typical operation, aluminum sulfate hydrate (alum) and sodium citrate dihydrate are dry blended, shipped to the well field, dispersed in water and pumped into the formation. Water dispersion of the dry blend at the well site is necessary due to the unavailability of a suitable method for the preparation of a stable water solution of aluminum citrate. This method suffers from several disadvantages. First of all, the solid ingredients dissolve slowly and often incompletely in water and the incompletely dissolved material can cause mechanical wear on seals and moving parts of injection pumps. Furthermore, there is no control over the pH of the solution which is corrosive at its normal pH of about 2.5. In addition, the use of alum introduces sulfate into the formation which when acted upon by sulfate reducing bacteria, results in the presence of corrosive quantities of $H_2S$.

British Patent Specification No. 1,598,709 discloses a tanning material prepared by dissolving 2.8 kg of citric acid monohydrate in 11 kg of $H_2O$ and adding this solution to 33 kg of an aqueous solution of $AlCl_3$ and $Al_2(SO_4)_3$ containing 11% Al as $Al_2O_3$ at a pH of 1.7. This solution is then adjusted to pH 4.1–4.2 by the addition of $H_2SO_4$ and sufficient NaOH to raise the pH to the desired level. A substantial amount of aluminum citrate prepared by this method stays in solution at the pH of about 4 which is suitable for use in the tanning industry but too acidic for use in enhanced oil recovery. Increasing the pH to that which would be suitable for use in an oil bearing formation is not satisfactory with this composition, which has a ratio of aluminum ion to citric acid molecule of 5.2:1.0, because at the higher pH most of the aluminum citrate precipitates out of solution thereby rendering the solution too dilute for commercially viable use in enhanced oil recovery. Furthermore, the high ratio of aluminum to citrate in this formulation results in the presence of unchelated aluminum which is undesirable in the gelling system under consideration because its presence causes rapid and uncontrolled cross-linking of the polymer. The maximum ratio of fully chelated aluminum to citrate is 2:1.

Grossmith, et al disclose in U.S. Pat. No. 3,391,176 compounds of the general formula:

$$M_x[M'_y(AO)_2(CH_3CO_1O)_w(OH)_{1x+w+y(m-2z)}(H_2O)_v]_n$$

where M is magnesium, calcium, sodium, potassium or ammonium and M' is aluminum, magnesium, iron or calcium and AO is the salicylato bidendate ion with Z being an integer of 1 to 4. The patentee's stated purpose for preparing these double salts is to provide a form of salylic acid which can be ingested without causing gastric distress.

Goldsmith in U.S. Pat. No. 3,200,136 and Niedercorn in U.S. Pat. No. 2,327,815 disclose the preparation of very dilute solutions of aluminum citrate having a molar ratio of aluminum ion to citric acid molecule of 1:1. Examples 5 of the '136 patent discloses a solid aluminum citrate with a ratio of 2:1 which has a solution pH of 3.

SUMMARY OF THE INVENTION

The present invention is a method for the preparation of an aqueous solution of an aluminum citrate complex which comprises the steps of:

(a) providing an aqueous solution of $AlCl_3$ containing up to about 34 weight % $AlCl_3$;

(b) combining the $AlCl_3$ solution with an aqueous solution of citric acid containing up to about 50 weight % citric acid, while vigorously agitating the resultant solution to form an aluminum citrate solution having a mole ratio of aluminum ion to citric acid molecule of from about 1.5:1 to about 2:1, said $AlCl_3$ solution being provided in an amount sufficient to form an aluminum citrate solution containing from 1 up to about 3 weight % aluminum; and (c) adding a basic hydroxide of the formula MOH where M is an alkali metal or ammonium cation to the aluminum citrate solution, while continuing to vigorously agitate the solution and while maintaining its temperature within the range of from 20° C. to 90° C., in sufficient quantity to raise the pH of the solution to a level of from 5.5 to 7.5.

DESCRIPTION OF THE INVENTION

The present invention provides the following advantages over the prior art method of dissolving a dry blend of aluminum sulfate and sodium citrate in water at the well site:

1. There are no solids in the solution to cause wear and tear on pumping equipment.
2. The aluminum citrate liquid can be shipped from the formulation site to the well site in tank trucks, stored in bulk and pumped into the formation when desired.
3. There is afforded complete control over the pH of the solution resulting in low corrosion rates and optimum gelling performance.
4. There is no manual handling of dry material required which results in a safer operation.
5. There is no opportunity for operator error since the product is complete as it arrives at the well site.

In each of the process steps, there have been discovered certain critical parameters which are necessary to the successful formation of a stable solution.

In a typical formulation, sufficient aluminum chloride is used to provide a mole ratio of aluminum to citric acid molecule of from about 1.5:1 to about 2:1. At higher ratios of aluminum ion to citric acid molecule, the solids will precipitate from solution at a pH level in the range suitable for use in enhanced oil recovery resulting in a drastically reduced amount of aluminum being made available to cross-link the polymer in the oil bearing formation. At a ratio below about 1.5:1, the time required to cross-link the polymer, as determined by the gelling rate, is unacceptably long. For maximum stability of the solution, a ratio of about 1.9:1 has been found to be preferable.

Aluminum chloride solutions containing up to about 34 weight % salt are commercially available. Since more concentrated solutions are not stable, this is the maximum practical concentration. Less concentrated solutions are suitable, but since it is desirable to provide an aluminum citrate solution which is highly concentrated yet stable, a concentrated (32° Be) solution is preferred. Likewise, it is desirable to use a citric acid solution which contains up to about 50 weight % citric acid, although less concentrated solutions can be employed. For economic reasons, it is desirable to provide an aluminum citrate solution having as high a concentration of aluminum as possible. A solution containing less than 1 weight % aluminum would be impractical because of the larger volume of solution which would be required to provide the needed amount of aluminum to the oil bearing formation. It has been discovered that the process of the present invention can be used to provide an aluminum citrate solution containing up to about 3 weight % aluminum. When mixing the aluminum chloride and citric acid solutions, it is essential that vigorous agitation be maintained throughout the process until a clear solution of aluminum citrate is achieved. At this point, the solution's pH is too low for compatibility with its use in the above-described enhanced oil recovery techniques because of the solution's tendency to be corrosive. Furthermore, the aluminum citrate is not very soluble at a lower pH in the ratio of aluminum ion to citric acid molecule desirable for enhanced oil recovery. The addition of an alkali metal or ammonium hydroxide is necessary to raise the pH to the desired level. This is accomplished by adding an aqueous solution of the basic material to the aluminum citrate solution in sufficient quantity to raise its pH to a level of from 5.5 to 7.5, preferably from 6.0 to 7.0. Alternatively, ammonia gas can be bubbled into the solution to form ammonium hydroxide in situ. When dry ammonia is used as the source of the base, some dilution of the aluminum citrate solution is desirable to avoid precipitation. Vigorous agitation of the solution is essential during the addition of the base to prevent precipitation of the aluminum already in solution in the form of aluminum hydroxide which will reduce the aluminum assay of the solution. In addition, temperature control is essential during this step due to the exothermic reaction which results upon addition of the base. The temperature should be maintained within the range of from 20° C. to 90° C. during this step with a temperature in the range of from 40° C. to 60° C. being preferred. Slow addition of the base together with external cooling have been found adequate to maintain the temperature within the desired range.

An aluminum citrate solution prepared in the above-described manner will remain stable for a period of from 10 to 14 days. It has been discovered that the period of stability can be increased by adding sufficient base to raise the pH to a level of 6.0 to 7.0 and then lowering the pH to a level of from 5.0 to 5.5 by the addition of a mineral acid, preferably HCl. However, in this embodiment, it is necessary to increase the pH from 5.0 to at least 5.5 before injecting the solution into the formation in order to achieve optimum results in the tertiary oil recovery procedure.

The method of practicing the present invention is further illustrated by the following examples:

EXAMPLE I

A 600 ml beaker was charged with 258 g of a commercially available 34 weight % AlCl$_3$ solution and 107.65 g of a 50% citric acid solution to provide a mole ratio of aluminum to citric acid of 2:1. The resulting solution was stirred vigorously for 35 minutes after which period 25 ml of a 50% NaOH solution was added via burette over a period of 36 minutes.

This procedure resulted in a liquid aluminum citrate having the following specifications:

| | |
|---|---|
| Aluminum Assay | = 2.9% w/w (3.7% w/v) |
| pH | = 6.8 |
| Sq. Gravity | = 1.295 |
| Freezing (crystallization point) | = −20° C. |

This solution remained stable for a period of approximately 2 weeks.

EXAMPLE II

The following experiment was run to develop a formulation based on 2.0 moles of Al to 1.1 mole of citric acid:

A 250 ml beaker was charged with 55 g of a 34% solution of aluminum chloride. To this was quickly added 25.3 g of a 50% (w/w) citric acid solution and 30.0 g of a 50% NaOH solution was added, while keeping the temperature at about 60° C., to bring the pH to 6.5. This procedure provided a crystal clear solution having a specific gravity of 1.293 which remained stable for approximately 2 weeks.

EXAMPLE III

The following procedure was carried out in a 21,196 liter fiberglass mix tank equipped with 10 coils of a 3.8 cm diameter polyvinyl chloride cooling coil, a turbine agitator and 1 air wand for additional agitation.

The procedure was as follows:

| Day 1 | |
|---|---|
| 4:30 p.m. | The tank was charged with 7,986 liters of a 34% aluminum chloride solution directly from a tank truck. |
| 7:30 p.m. | Citric acid, 3.857 liters of a 50% (w/w) solution, was added while maintaining vigorous agitation. |
| 9:00 p.m. | Slow addition of a 50% (w/w) NaOH solution was commenced with external cooling of the vat. At this point, the pH was less than 1 and the temperature was 55° C. Addition of the sodium hydroxide was continued for approximately 18 hours under the following schedule: |

| Day 2 | Temperature | pH |
|---|---|---|
| 7:30 a.m. | 55° C. | — |
| 4:00 p.m. | 53° C. | 1.24 |
| 8:30 p.m. | 54° C. | 2.76 |
| 12:00 midnight | 54° C. | 4.72 |

| Day 3 | Temperature | pH |
|---|---|---|
| 12:18 a.m. | 54° C. | 5.39 |
| 12:44 a.m | 55° C. | 6.05 |
| 1:01 a.m. | 55° C. | 6.20 |
| 1.15 a.m. | 55° C. | 6.40 |
| 1:30 a.m. | — | 6.57 |

By the time the desired pH was achieved, the total amount of NaOH added was 3,709 liters. This procedure provided 15,140 liters of liquid aluminum citrate containing 2.97% (w/w) aluminum.

After 2 weeks, a sample of the material became cloudy. Analysis of the clear supernatant showed 2.74% (w/w) aluminum indicating that 7.7% of the original aluminum had precipitated out.

EXAMPLE IV

A 600 ml beaker was charged with 169.6 g of AlCl$_3$ (32° C.-11.03 g Al) or 0.409 mole. To this was added 82.6 g of 50% citric acid (41.3 g citric acid/0.215 mole). With agitation, the resultant was slowly neutralized to the pH level shown in the following table by adding 50% NaOH dropwise while keeping the temperature between 40° C. and 55° C. At each pH value, the volume of precipitate and the amount of aluminum in solution, as determined by atomic absorption assay, were recorded. This material exhibited the following solubility at the various pH levels:

| pH | Al in Solution | Volume of Ppt. |
|---|---|---|
| 5.5 | 35,000 ppm | 0% |
| 6.0 | 33,000 | 0 |
| 6.5 | 34,000 | 0 |
| 7.0 | 33,000 | 0 |

Following the procedure of British Patent Specification No. 1,598,709, a 250 ml beaker was charged with 5.12 g of anhydrous citric acid (0.27 mole) and 22.48 g of distilled water with stirring until the citric acid had dissolved. To this was added 33 g of AlCl$_3$ solution (32° C. Be) and 33 g of an Al$_2$(SO$_4$)$_3$ solution containing 17% Al$_2$O$_3$ which was then stirred for 5 minutes. This provided a total of 0.141 mole of aluminum ion. At this point, there was added 10 g of concentrated H$_2$SO$_4$ and 32 g of distilled water and the resultant was neutralized slowly to a pH of 4.0 by the addition of 83.5 ml of 20% NaOH with agitation while maintaining the temperature of the solution below 35° C. The amount of aluminum in solution and volume of precipitate was determined at each 0.5 pH unit as the pH was increased from 4.0 to 7.0 with the results being reported in the following table:

| pH | Al in Solution | Volume of Ppt. |
|---|---|---|
| 4.0 | 16,800 ppm | 0% |
| 4.5 | 14,800 | 16 |
| 5.0 | 13,600 | 23 |
| 5.5 | 1,200 | 94 |
| 6.0 | 800 | 93 |

-continued

| pH | Al in Solution | Volume of Ppt. |
|---|---|---|
| 6.5 | 500 | 100 |
| 7.0 | 400 | 89 |

The prior art method calls for stopping the neutralization of the aluminum citrate solution at pH 4.2 at which point the solution is clear. This pH, however, is too low for the proper cross-linking of polymers and results in a weak, unstable gel. Raising the pH to the range of 5.5 to 7.5 causes the aluminum to precipitate out rendering the material unsuitable for the intended purpose.

EXAMPLE V

A performance test for determining the ability of aluminum citrate to cross-link polymers which has been accepted by many major oil producing concerns is conducted as follows:

Procedure

1. Acidify 100 ml of carboxymethyl cellulose (CMC) solution (5,000 ppm CMC in 1% KCl solution) in a 250 ml beaker to pH 3.5 using 15% HCl.
2. Add 3.3 ml±3% Al of aluminum citrate solution using more than 3.3 ml if concentration of Al is less than 3%.
3. Stir until homogeneous. The pH of the combination of the polymer and aluminum citrate solution is about pH 4.5. This pH is lower than one would prefer to encounter in an oil bearing formation because it results in too rapid gel formation. However, a low pH and consequent rapid gel formation has been found to be desirable for this accelerated test.
4. Pour into ca. 1 inch diameter glass test tube.
5. Record firm gel time as no air bubble rising when inverting test tube.
6. Acceptable material gels in less than 30 minutes. Most will gel in less than 15 minutes.

Using this procedure, the gelling times for aluminum citrate solutions having ratios of aluminum ion to citric acid molecule of from 1.0:1.0 to 2.0:1.0 were obtained. The results of this experiment are set out in the following table:

| Al to Citrate Molar Ratio | Gel Test Time |
|---|---|
| 2.0 Al:1.0 Citrate | 1 minute |
| 1.9:1.0 | 1 |
| 1.8:1.0 | 2 |
| 1.7:1.0 | 5 |
| 1.6:1.0 | 17 |
| 1.5:1.0 | 12 |
| 1.4:1.0 | 3 hours |
| 1.3:1.0 | 16 |
| 1.2:1.0 | No gel in 3 days |
| 1.1:1.0 | No gel in 3 days |
| 1.0:1.0 | No gel in 3 days |

From the above data, it can be determined that an aluminum citrate solution with a mole ratio of aluminum ion to citric acid molecule of at least about 1.5:1 is necessary for the satisfactory cross-linking of carboxymethylcellulose which is a preferred cross-linkable polymer for use in enhanced oil recovery.

What is claimed is:

1. A method for the preparation of an aqueous solution of an aluminum citrate complex which consists essentially of the following steps:
   (a) providing an aqueous solution of $AlCl_3$ containing up to about 34 weight % $AlCl_3$;
   (b) combining the $AlCl_3$ solution with an aqueous solution of citric acid containing up to about 50 weight % citric acid, while vigorously agitating the resultant solution, to form an aluminum citrate solution having a mole ratio of aluminum ion to citric acid molecule of from about 1.5:1 to 2.0:1, said $AlCl_3$ solution being provided in an amount sufficient to form an aluminum citrate solution containing from 1 up to about 3 weight % aluminum; and
   (c) adding a basic hydroxide of the formula MOH where M is an alkali metal or ammonium cation to the aluminum citrate solution, while continuing to agitate the solution and while maintaining its temperature within the range of from 20° C. to 90° C., in sufficient quantity to raise the pH of the solution to a level of from 5.5 to 7.5.

2. The method of claim 1 wherein the mole ratio of aluminum ion to citric acid is about 1.9:1.

3. The method of claim 1 wherein the temperature is maintained at a level of from 40° C. to 60° C. during the addition of the basic hydroxide.

4. The method of claim 1 wherein the basic hydroxide is NaOH.

5. The method of claim 4 wherein the NaOH is added in the form of its 50% (w/w) aqueous solution.

6. The method of claim 1 wherein sufficient basic hydroxide is added to raise the pH to a level of from 6.0 to 7.0.

7. A method for the preparation of a stable liquid aluminum citrate which consists essentially of the following steps:
   (a) providing an aqueous solution of aluminum chloride containing up to about 34% (w/w) of aluminum chloride;
   (b) combining the aluminum chloride solution with an aqueous solution of citric acid containing up to about 50% (w/w) citric acid while providing vigorous agitation to form a solution of aluminum citrate containing from 1 to about 3 weight % aluminum and having a mole ratio of aluminum ion to citric acid molecule of from about 1.5:1 to about 2:1; and
   (c) adding a 50% (w/w) solution of sodium hydroxide to the aluminum citrate solution, while continuing to provide vigorous agitation and maintaining the temperature of the resultant at a level of from 40° C. to 60° C., to raise the pH to a level of from 6.0 to 7.0.

* * * * *